(12) United States Patent
Ham et al.

(10) Patent No.: US 10,799,547 B2
(45) Date of Patent: Oct. 13, 2020

(54) COMPOSITION COMPRISING SUAEDA JAPONICA FOR PREVENTING OR ALLEVIATING DIABETES

(71) Applicant: Mokpo National University Industry-Academia Cooperation Group, Jeollanam-do (KR)

(72) Inventors: Kyung Sik Ham, Gwangju (KR); Jeong Yong Cho, Gwangju (KR); Sun Young Park, Jeollanam-do (KR); Zhangjun Huang, Jeollanam-do (KR)

(73) Assignee: MOKPO NATIONAL UNIVERSITY INDUSTRY-ACADEMIA COOPERATION GROUP, Jeollanam-Do (KR)

( * ) Notice: Subject to any disclaimer, the term of this patent is extended or adjusted under 35 U.S.C. 154(b) by 113 days.

(21) Appl. No.: 14/651,529

(22) PCT Filed: Jul. 23, 2013

(86) PCT No.: PCT/KR2013/006594
§ 371 (c)(1),
(2) Date: Nov. 23, 2015

(87) PCT Pub. No.: WO2014/077487
PCT Pub. Date: May 22, 2014

(65) Prior Publication Data
US 2016/0067294 A1    Mar. 10, 2016

(30) Foreign Application Priority Data

Nov. 19, 2012   (KR) .................. 10-2012-0130701

(51) Int. Cl.
| | | |
|---|---|---|
| *A61K 36/00* | (2006.01) | |
| *A61K 36/21* | (2006.01) | |
| *A61K 9/14* | (2006.01) | |
| *A23L 33/105* | (2016.01) | |
| *A23L 2/02* | (2006.01) | |
| *A23L 2/52* | (2006.01) | |
| *A61K 9/00* | (2006.01) | |
| *A61K 47/36* | (2006.01) | |

(52) U.S. Cl.
CPC .............. *A61K 36/21* (2013.01); *A23L 2/02* (2013.01); *A23L 2/52* (2013.01); *A23L 33/105* (2016.08); *A61K 9/0095* (2013.01); *A61K 9/14* (2013.01); *A61K 47/36* (2013.01); *A23V 2002/00* (2013.01)

(58) Field of Classification Search
CPC ..................................................... A61K 36/00
USPC ........................................................ 424/725
See application file for complete search history.

(56) References Cited

U.S. PATENT DOCUMENTS

2001/0021408 A1* 9/2001 Kim .................. A23L 27/40
426/640

FOREIGN PATENT DOCUMENTS

| KR | 804410 | * 2/2008 |
|---|---|---|
| KR | 10-0911623 | 8/2009 |

OTHER PUBLICATIONS

Benwahhoud et al., (2001). "Hypoglycemic effect of suaeda fruticosa in streptozotocin-induced diabetic rats." *Journal of Ethnopharmacology*. 76:35-38 (see the entire document).
Hwang (2012). "Effects of various halophytes on insulin resistance and diabetes in Otsuka long-evans tokushima fatty (OLETF) rats." *Thesis(M.A.)—Graduate School, Mokpo National Univ. Dept. of Food Engineering*. pp. 6, 78-79(abstract).
Kavishankar et al., (2011). "Diabetes and medicinal plants—A review." *Int J Pharm Biomed Sci*, 2(3):65-80.
International Search Report (ISR) dated Jul. 23, 2013 in PCT/KR2013/006594, with English translation.

* cited by examiner

*Primary Examiner* — Michael V Meller
(74) *Attorney, Agent, or Firm* — Harness, Dickey & Pierce, P.L.C.

(57) ABSTRACT

The present invention relates to a food composition comprising *Suaeda japonica* as an active ingredient for preventing or alleviating diabetes, and to a method for preparing the composition. When *Suaeda japonica* powder of the present invention is administered to OLETF mice in which obesity and diabetes are naturally induced during growth due to a defect of the CCK-1 gene, an increase in blood glucose and production of glycosylated hemoglobin are inhibited, and the effect of improving glucose tolerance is exhibited. Also, a high blood level of adiponectin, which relates to an improvement in insulin sensitivity and to the recovery of glucose metabolism function, is maintained, and antidiabetic activity, specifically, the effect of alleviating or preventing diabetes, is excellent.

1 Claim, 7 Drawing Sheets

COMPOSITION COMPRISING SUAEDA JAPONICA FOR PREVENTING OR ALLEVIATING DIABETES

CROSS-REFERENCE TO RELATED APPLICATIONS

This application is a national phase application of PCT Application No. PCT/KR2013/006594, filed on 23 Jul. 2013, which claims benefit of Korean Patent Application 10-2012-0130701, filed on 19 Nov. 2012. The entire disclosure of the application identified in this paragraph is incorporated herein by reference.

FIELD

The present invention relates to a composition for preventing or alleviating diabetes and a method of preparing the same, and more particularly, to a composition including a natural substance or a natural extract as a main ingredient for preventing or alleviating diabetes.

BACKGROUND

Diabetes means a disease in which glucoses are discharged in the urine because blood sugar is not controlled without using sugar in the blood when a balance between vivo insulin sensitivity and insulin secretion is broken, that is, when the insulin is deficient or the insulin sensitivity is reduced.

The diabetes is largely divided into a first type of diabetes and a second type of diabetes. The first type of diabetes, that is, Insulin-dependent diabetes' is caused by reducing generation and secretion of insulin by the damage of pancreatic β-cells secreting the insulin. In order to treat the first type of diabetes, generally, blood glucose is reduced by administrating insulin from outside. The second type of diabetes, that is, Insulin-independent diabetes' means a state in which the blood glucose is increased over a normal and is caused when a balance between reduction of insulin action in peripheral tissues of muscle, fat, and liver and secretion of insulin in the pancreas is broken. Most diabetes patients exhibit insulin resistance and hyperinsulinemia before proceeding to the second type of diabetes. That is, in the second type of diabetes, the action of insulin reducing initial blood glucose deteriorates, insulin resistance in which glucose is not effectively absorbed so as not to be used as energy in the peripheral tissues occurs, and as a result, hyperinsulinemia in which an insulin secretion rate is increased in order to reduce the caused high blood glucose is exhibited. If the hyperinsulinemia is not overcome, the hyperinsulinemia proceeds to the second type of diabetes. In Korea, the number of patients of the second type of diabetes has been increased for the last 10 years.

It is understood that an increase in a diabetes prevalence rate is caused by economic growth and changes in eating habits and lifestyles according to industrialization, race or family history factors, an increase in an obesity rate, and the like.

In the diabetes patient, it is important to maintain normal blood glucose by a diet or a drug. However, in the second type of diabetes, even though non-pharmacological treatment is performed through a diet and exercise, the blood glucose is not easily controlled in some cases, and in this case, administration of an oral hypoglycemic agent or insulin is required. However, in the oral hypoglycemic agent which is frequently used, hypoglycemia may be caused as side effects due to exhaustion of beta cells and side effects such as lactic acidosis are caused. Further, an insulin injection is inconvenient in use and has a difficulty in a long-term blood glucose control because obesity is promoted when being used for a long time if there is the risk of hypoglycemia. Accordingly, a need to develop naturally derived anti-diabetes materials in few side effects are exhibited in the second type of diabetes patients and administration is easy has been increased.

RELATED ART

Patent Documents (Patent Document 1) Patent application No. 2009-0003025
(Patent Document 2) Patent application No. 2009-0099386
(Patent Document 3) Patent application No. 2009-0124988
(Patent Document 4) Patent application No. 2006-0062328

SUMMARY

Technical Problem

The present invention is created for improving the problems in the related art and satisfying requirements related with the treatment of the diabetes, and an object of the present invention is to provide an active ingredient of a food composition including a natural substance for preventing or alleviating the diabetes with few side effects while having an effect on maintaining a high level of the blood insulin and improving glucose tolerance, that is, reducing insulin resistance.

Technical Solution

A composition for preventing or alleviating diabetes according to an embodiment of the present invention includes *Suaeda japonica*.

The *Suaeda japonica* may be *Suaeda japonica* powder, and the *Suaeda japonica* powder may correspond to a spray-dried substance of a *Suaeda japonica* juice.

A composition for protecting pancreatic β-cells according to another embodiment of the present invention includes *Suaeda japonica*, and the *Suaeda japonica* may have any one form of powder or liquid.

A method of preparing *Suaeda japonica* juice powder according to yet another embodiment of the present invention includes: removing foreign substances by washing *Suaeda japonica*; preparing a juice extraction by juice-extracting the *Suaeda japonica* from which the foreign substances are removed by using a juice extractor; preparing a mixture by adding dextran to the juice extraction; and obtaining powder by spraying and drying the mixture.

Advantageous Effects

As described above, the *Suaeda japonica*, particularly, the *Suaeda japonica* juice powder prepared by the present invention has an excellent effect of treating or preventing the diabetes including reducing the blood glucose, increasing an insulin secretion rate, improving glucose tolerance, and increasing the content of adiponectin in the blood as a result verified through a change in the blood glucose, the glucose tolerance, and the blood adiponectin content. In addition, the *Suaeda japonica* as the active ingredient of the food composition for treating or preventing the diabetes is used as the food, that is, derived from the natural substance and thus, problems such as side effects do not occur.

Further, according to the present invention, it is possible to provide a technique capable of having a more fundamental ripple effect by providing a causal relationship between the efficacy of the *Suaeda japonica* and an effect of inhibiting the diabetes and providing an inhibition effect on pancreatic β-cells destruction by the *Suaeda japonica*.

DETAILED DESCRIPTION

Hereinafter, a composition for preventing or alleviating diabetes will be described in detail.

In the present invention, *Suaeda japonica* as an annual plant of chenopodiaceae is a halophyte which grows naturally in the intertidal region of the southwest coast in Korea. The *Suaeda japonica* has various colors from green to red according to a growth time, and the shape is similar to a turkey to be called *Suaeda japonica*. The *Suaeda japonica* has red to be used as natural salt such as promlmence which is vegetable salt and an aerial part has been used as a fever reducer in oriental medicine. It is known that the *Suaeda japonica* has a high-concentration NaCl content and plenty of minerals such as magnesium, calcium, and potassium. As researches on biological activity of the *Suaeda japonica*, it is reported that there is an antioxidative effect, and the researches on a variety of biological activity and active ingredients are very insufficient. The *Suaeda japonica* is widely distributed in the intertidal region such as mudflats and salt marshes unlike other halophytes including salicomia herbacea having low yield.

The *Suaeda japonica* may be *Suaeda japonica* juices, *Suaeda japonica* powders, *Suaeda japonica* juice powders, or *Suaeda japonica* extracts, and preferably, the *Suaeda japonica* juice powder.

The juice extraction of the present invention means a liquid juice separated from a solid or semifluid material as a process used in a food preparing process and the like or a product thereof. The juice extraction may be prepared by a general method of preparing a general plant juice extraction, and as an example, the juice extraction may be prepared by using a juice extractor such as a piston press type, a screw press type, an expansion press type, a tubular type, and a centrifugal type, and the like or a method of crushing and juice extraction.

Figure 1:
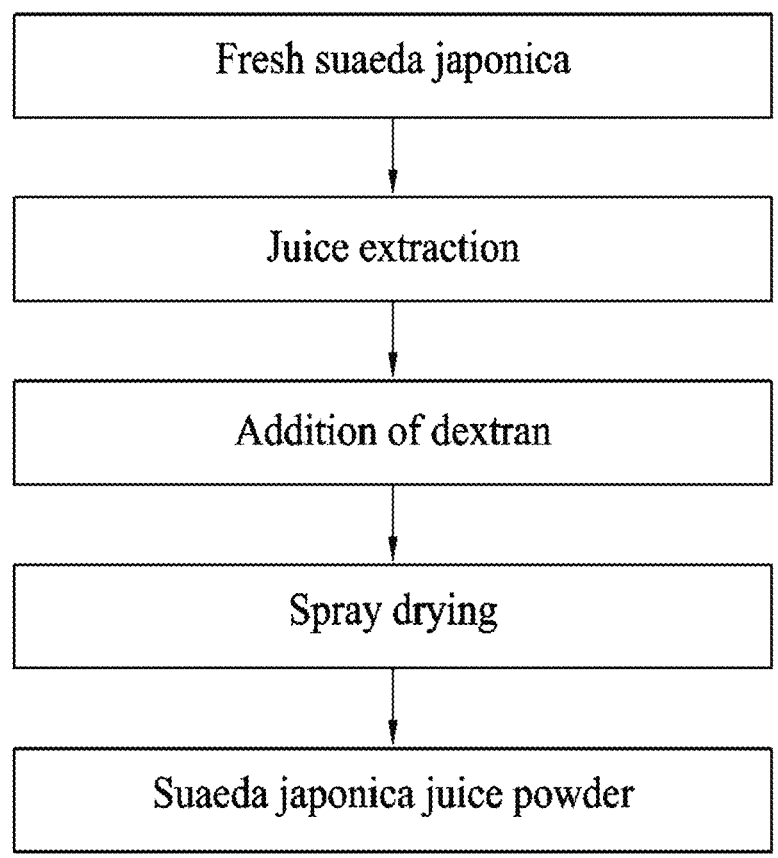
FIG. 1 is a flowchart schematically illustrating a method of preparing *Suaeda japonica* juice powder having an effect of preventing diabetes according to an embodiment of the present invention.

The powder of the present invention means a general name of finely crumbled grains or flour and may be particularly prepared by a method illustrated in FIG. 1.

The powder may be prepared by a general method of preparing a general plant powder and as an example, may be prepared by a method of grinding the plant after drying or spraying and drying a plant juice extraction through a spray method and the like.

The extract of the present invention may be prepared by being extracted with an extractant or fractionated by adding a fraction solvent to a crude extract prepared by being extracted with the extractant.

The extractant may be one or more kinds selected from a group consisting of water and an organic solvent. The organic solvent may be an alcohol having carbon atoms 1 to 5 such as methanol and ethanol, a polar solvent such as ethylacetate or acetone, a nonpolar solvent such as ether, chloroform, benzene, hexane, or dichloromethane, or a mixed solvent thereof.

The extract of the present invention may be prepared by a method of preparing an extract to be extracted with a general terrestrial plant, preferably, leaves or seeds, and particularly, the method may be a macerating extraction method, a digesting extraction method, a thermal extraction method, or the like and use a general extractor, an ultrasonic mill extractor, or a fraction machine. In the prepared extract, thereafter, the solvent may be removed by performing filtering, concentrating, or drying process, and all of filtering, concentrating, and drying may be performed. In detail, the filtering may be performed by using a filter paper or a decompression filter, the concentrating may perform decompression concentration by using, for example, a rotary evaporator, and the drying may be performed by, for example, a freeze-drying method or a spray-drying method.

As an example of the present invention, the *Suaeda japonica* juice powder may be obtained by the method illustrated in FIG. 1.

In more detail, the *Suaeda japonica* juice powder may be prepared by removing mud and foreign substances by washing the *Suaeda japonica* in flowing water, juice-extracting the washed *Suaeda japonica* by a juice extractor to obtain a juice extraction, and then adding, spraying, and drying dextran to the juice extraction.

The present invention relates to a composition including *Suaeda japonica*, preferably, a *Suaeda japonica* juice powder as an active ingredient for treating or preventing diabetes.

In the present invention, the diabetes means a disease in which glucoses are discharged in the urine because blood glucose is not controlled without using sugar in the blood when a balance between vivo insulin sensitivity and insulin secretion is broken, that is, when the insulin is deficient or the insulin sensitivity is reduced. The diabetes is largely divided into a first type of diabetes and a second type of diabetes, and the diabetes may be preferably the second type of diabetes.

The composition including the *Suaeda japonica* as the active ingredient for treating or preventing the diabetes according to the present invention may include the *Suaeda japonica* juice powder of 0.001 to 99.99 wt %, preferably, 0.1 to 99 wt % with respect to a total weight of the composition.

The composition including the *Suaeda japonica* as the active ingredient for treating or preventing the diabetes according to the present invention does not cause a problem of side effects in that the active ingredient of the composition is a natural substance, particularly, a juice extraction of the natural substance, a powder of the natural substance, or an extract of the natural substance and has an excellent effect in that there is an effect of alleviating or preventing the diabetes.

The composition including the *Suaeda japonica* as the active ingredient for treating or preventing the diabetes according to the present invention may be directly applied to the human.

The composition including the *Suaeda japonica* juice powder as the active ingredient for treating or preventing the diabetes may include the *Suaeda japonica* juice powder as the active ingredient alone, and additionally include an additional component, that is, a carrier, an excipient, a diluent, or a sub component which is pharmaceutically acceptable or nutritionally acceptable according to a formulation, a use method, and a use purpose in addition to the active ingredient.

In more detail, the composition including the *Suaeda japonica* juice powder as the active ingredient for treating or preventing the diabetes may additionally include a nutrient, a vitamin, an electrolyte, a flavoring agent, a coloring agent, an enhancer, pectic acid and salt thereof, alginic acid and salt thereof, organic acid, a protective colloidal thickener, a pH adjusting agent, a stabilizer, a preservative, glycerin, alcohol, a carbonic acid agent used in a carbonated drink, or the like in addition to the active ingredient. Further, the carrier, the excipient, or the dilute may be one or more selected from a group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate and mineral oil, dextrin, calcium carbonate, propylene glycol, liquid paraffin, and normal saline, but is not limited thereto and may use all of general carriers, excipients, or dilutes. The components may be added to the *Suaeda japonica* juice powder as the active ingredient independently or in combination.

The composition including the *Suaeda japonica* as the active ingredient for treating or preventing the diabetes may include the *Suaeda japonica* having 0.001 wt % to 99.9 wt %, preferably, 0.1 wt % to 99 wt %, and more preferably 1 wt % to 50 wt % with respect to the total weight of the composition. Further, the content of the additional component may be preferably added in a range of 0.1 to 20 parts by weight per 100 parts by weight of the composition for treating or preventing the diabetes.

Further, when the composition including the *Suaeda japonica* as the active ingredient for treating or preventing the diabetes is made of a pharmaceutical product, the composition may further include a general filler, an extender, a binder, a disintegrating agent, a surfactant, an anti-coagulant, a lubricant, a wetting agent, a flavoring agent, an emulsifier, or a preservative, and be used orally or parenterally.

In detail, a solid formulation for oral administration includes a tablet, a pill, a powder, a granule, a capsule, or the like, and the solid formulation may be prepared by mixing at least one excipient, for example, starch, calcium carbonate, sucrose or lactose, gelatin, or the like with the *Suaeda japonica* juice powder. Further, lubricants such as magnesium stearate and talc may be used in addition to simple excipients. A liquid formulation for oral administration may use a suspension, a solution, an emulsion, a syrup, and the like, and may include various excipients, for example, a wetting agent, a sweetener, an aromatic agent, a preserving agent, and the like in addition to water and liquid paraffin which are commonly used as simple diluents.

Further, the formulation of the composition including the *Suaeda japonica* as the active ingredient for treating or preventing the diabetes according to the present invention may be a preferable form according to a use method, and particularly, the formulation may be performed by adopting a method known in the art so as to provide rapid, contiguous, or delayed release of the active component after being administrated to a mammal. A detailed example of the formulation includes a granule, a powder, a syrup, a solution, a suspension, a tablet, an injection, an alcoholic, a cataplasma, a capsule, a soft or hard gelatin capsule, or the like.

Furthermore, the composition including the *Suaeda japonica* as the active ingredient for treating or preventing the diabetes according to the present invention may be preferably formulated by using an appropriate method known in the art or a method disclosed Remington's literature (Remington's Pharmaceutical Science (the latest issue), Mack Publishing Company, Easton Pa.).

An administration amount of the composition including the *Suaeda japonica* as the active ingredient for treating or preventing the diabetes according to the present invention may be properly selected by those skilled in the art by considering an administrating method, an age, a sex, and a weight of a taker, the severity of the disease, and the like. As an example, the composition including the *Suaeda japonica* as the active ingredient for treating or preventing the diabetes according to the present invention may be administrated with 0.0001 mg/kg to 1,000 mg/kg, more effectively, 0.01 mg/kg to 100 mg/kg based on the *Suaeda japonica*. The administration may be performed once a day or several times. The administration amount does not limit the scope of the present invention in any aspect.

Further, the composition including the *Suaeda japonica*, preferably, the *Suaeda japonica* juice powder as the active ingredient for treating or preventing the diabetes according to the present invention may further include a known compound having an effect of treating or preventing the diabetes or an extract for the natural substance other than the *Suaeda japonica*, and the compound or the extract for the natural substance may be included with 5 parts by weight to 200 parts by weight with respect to 100 parts by weight of the *Suaeda japonica* juice powder.

Further, in order to achieve the object, the present invention provides a food composition including *Suaeda japonica*, preferably, a *Suaeda japonica* juice powder as an active ingredient for preventing or alleviating diabetes.

In this specification, the food means natural substances or processed products including one or more nutrients and preferably, means a state which may be directly eaten through a certain processing process, and as a general meaning, includes health food, beverage, food additives, beverage additives, and the like.

The food of the present invention includes, for example, such as various foods, beverages, chewing gum, tea, vitamin complex, and health food. Additionally, the foods in the present invention include special nutritious foods (for example, preparation oil, baby food, and the like), meat products, fish products, tofu, muk, noodles (for example, ramen, noodles, and the like), dietary supplements, flavoring food (for example, soy sauce, soybean paste, red pepper paste, mixed paste, and the like), sauces, confectionery (for example, snacks), milk products (for example, fermented milk, cheese, and the like), other processed foods, kimchi, pickled food (all kinds of Kimchi, pickle, and the like), beverages (for example, fruit and vegetable beverages, soybean milk, fermented beverages, and the like), and natural seasonings (for example, ramen soups, and the like), but are not limited thereto. The food, the health food, the beverage, the food additives, and the beverage additives may be prepared by general preparing methods.

In the present invention, the health food means foods designed and processed to sufficiently express a body control function in the body regarding bio-defense rhythm control, prevention and recovery of the disease, and the like of a food group or a food composition given with added value so as to act and express functions of the corresponding food according to a specific purpose by using physical, biochemical, biotechnological techniques in the food.

The health food may include food aid additives which are cytologically acceptable and further include appropriate carriers, excipients, and dilutes which are generally used in the preparation of the health food.

In the present invention, the beverage means a collective term for drinks for quenching thirst or enjoying the taste and includes healthy beverages. The beverage includes the *Suaeda japonica* juice powder as the active ingredient as an essential component with an indicated ratio and is not particularly limited to other components, and may include various flavoring agents or natural carbohydrates as an additional component like a general beverage.

Examples of the natural carbohydrates are general sugars such as monosaccharides, for example, glucose, fructose, and the like, disaccharides, for example, maltose, sucrose, and the like, and polysaccharides, for example, dextrin, cyclodextrin, and the like, and sugar alcohols such as xylitol, sorbitol, and erythritol. As the flavoring agents other than the above examples, natural flavoring agents (thaumatin, *stevia* extract (for example, rebaudioside A, glycyrrhizin, and the like) and synthetic flavoring agents (saccharin, aspartame, and the like) may be advantageously used. A ratio of the natural carbohydrate may be generally about 1 to 20 g and preferably 5 to 12 g per 100 of the food composition of the present invention. Moreover, the composition of the present invention may additionally include flesh for preparing natural fruit juices, fruit juice beverages, and vegetable beverages.

The food composition of the present invention may additionally include various nutrients, vitamins, minerals (electrolytes), flavoring agents such as a synthetic flavoring agent and a natural flavoring agent, coloring agents, enhancers (cheese, chocolate, and the like), pectic acid and salt thereof, alginic acid and salt thereof, organic acid, a protective colloidal thickener, a pH adjusting agent, a stabilizer, a preservative, glycerin, alcohol, a carbonic acid agent used in a carbonated drink, or the like in addition to the composition. The components may be used independently or in combination. The ratio of the additive is not important, but may be selected in a range of 0 to 2,000 parts by weight per 100 parts by weight of the *Suaeda japonica* juice powder of the present invention.

In the present invention, the healthy beverage means beverages designed and processed to sufficiently express a body control function in the body regarding bio-defense rhythm control, prevention and recovery of the disease, and the like of a beverage group or a beverage composition given with added value so as to act and express functions of the corresponding beverage according to a specific purpose by using physical, biochemical, biotechnological techniques in the beverage.

The healthy beverage includes the *Suaeda japonica* juice powder as the active ingredient as an essential component with an indicated ratio and is not particularly limited to other components, and may include various flavoring agents or natural carbohydrates as an additional component like a general beverage.

Examples of the natural carbohydrates are general sugars such as monosaccharides, for example, glucose, fructose, and the like, disaccharides, for example, maltose, sucrose, and the like, and polysaccharides, for example, dextrin, cyclodextrin, and the like, and sugar alcohols such as xylitol, sorbitol, and erythritol. As the flavoring agents other than the above examples, natural flavoring agents (thaumatin, *stevia* extract (for example, rebaudioside A, glycyrrhizin, and the like) and synthetic flavoring agents (saccharin, aspartame, and the like) may be advantageously used. A ratio of the natural carbohydrate may be generally about 1 to 20 g and preferably 5 to 12 g per 100 of the composition of the present invention.

Further, in the food composition including the *Suaeda japonica*, preferably, the *Suaeda japonica* juice powder as the active ingredient for preventing or alleviating the diabetes, an amount of the *Suaeda japonica* juice powder may include 0.01 to 15 wt % of the entire food weight and the beverage composition may be included with a ratio of 0.02 to 5 g, preferably, 0.3 to 1 g based on 100.

It was verified that the *Suaeda japonica* of the present invention has the effect of treating or preventing the diabetes including reducing the blood glucose, increasing an insulin secretion rate, improving glucose tolerance, and increasing the content of adiponectin in the blood as a result verified through a change in the blood glucose, the glucose tolerance, and the blood adiponectin content.

Further, the present invention relates to a method of preparing *Suaeda japonica* juice powder for alleviating or preventing diabetes including: removing foreign substances by washing the *Suaeda japonica*; preparing a juice extraction by juice-extracting the *Suaeda japonica* from which the foreign substances are removed by using a juice extractor; preparing a mixture by adding dextran to the juice extraction; and removing powder by spraying and drying the mixture.

Meanwhile, as the studied result, it is verified that the *Suaeda japonica* according to the present invention has a protective effect on pancreatic β-cells destruction caused from the second type of diabetes, and it will be described below through the detailed embodiment.

Hereinafter, a method of preparing the *Suaeda japonica* juice powder will be described in detail according to the detailed embodiment.

EXAMPLES

Example 1

Preparation of *Suaeda japonica* Juice Powder

*Suaeda japonica* used in Example 1 grows wild in the coast, Taean-gun, Chungcheongnam-do and *Suaeda*

*japonica* juice powder was prepared from the *Suaeda japonica* by using a method illustrated in FIG. 1.

In detail, the *Suaeda japonica* collected in October, 2010 was washed with water to remove mud and foreign substances. Dextran was added to a juice extraction obtained by juice-extracting the washed *Suaeda japonica* by using a juice extractor and spray-dried by using a spray drier to prepare the *Suaeda japonica* juice powder. FIG. 1 is a flowchart schematically illustrating preparation of a composition including the *Suaeda japonica* juice powder having an effect of preventing diabetes.

Verification of Anti-Diabetes Effect Using Experimental Animal

Mice used for evaluating an anti-diabetes effect of the *Suaeda japonica* juice powder prepared in Example 1 were OLETF mice in which obesity and the second type of diabetes were caused by continuous overeating while growing due to an innate defect of cholecystokinin (CCK-A) receptor genes. In the verification of the blood glucose suppression effect, a diabetes preventing effect of the *Suaeda japonica* juice powder was evaluated through analysis of a change in blood glucose and diabetes-related factors by ingesting the *Suaeda japonica* juice powder in OLETF mice at an age of 26 weeks when the diabetes was caused for 12 weeks.

Breeding of Experimental Animal

As experimental animals used in the present invention, OLETF mice at an age of 5 weeks were purchased from Otsuka corporation (Tokushima, Japan), and the experimental animals were bred up to an age of 26 weeks in a breeding room in which temperature (25.1° C.), humidity (50 to 60%), and illumination at a period of 12 hours (day and night, a period of 12 hours) were adjusted. Next, the OLETF mice were divided into two experimental groups (n=8) by a randomized block method to have similar weights and freely took water and a diet. Feed used in the breeding was prepared by adding the *Suaeda japonica* juice powder of 3 wt % of the entire feed to a basic composition of AIN-93G and the diet was performed by using the feed added with the *Suaeda japonica* juice powder for 12 weeks.

A weight and a dietary intake amount were performed once a week and a water intake amount was performed once a day for the diet period.

Verification of Change in Weight of Experimental Animals

Changes in dietary intake amount, water intake amount, and weight for the experimental animals were measured and listed in the following Table 1.

TABLE 1

| Age (week) (diet period, week) | Dietary intake amount (g/day) | | Water intake amount (mL/day) | | Weight (g) | |
|---|---|---|---|---|---|---|
| | Control group | *Suaeda japonica* juice powder-diet group | Control group | *Suaeda japonica* juice powder-diet group | Control group | *Suaeda japonica* juice powder-diet group |
| 26(0) | 31.1 | 31.1 | 69.6 | 69.6 | 628.5 | 630.7 |
| 28(2) | 29.6 | 29.0 | 73.3 | 50.9 | 652.7 | 651.5 |
| 30(4) | 26.1 | 26.9 | 102.5 | 65.6 | 654.7 | 651.5 |
| 32(6) | 28.2 | 27.6 | 108.4 | 80.99.3 | 624.1 | 653.9 |
| 34(8) | 31.0 | 28.2 | 131.3 | 79.4 | 606.0 | 660.6 |
| 36(10) | 32.4 | 27.7 | 191.3 | 115.0 | 586.0 | 657.9 |
| 38(12) | 32.4 | 27.8 | 193.1 | 126.3 | 556.4 | 641.6 |

As listed in Table 1, in the case of a control group bred by using feed with the *Suaeda japonica* juice powder is not mixed as a diet, the dietary intake amount was slightly decreased up to an age of 30 weeks (diet 4 weeks) and then continuously increased for the diet period. Further, the water intake amount was continuously increased for the diet period. Generally, it was known that OLETF mice were born with an innate defect of CCK-A involved in the action such as concentration in the gallbladder juice, the secretion of digestive enzymes from the pancreas, and absorption of nutrients in the small intestine and thus, obesity and the second type of diabetes were caused due to overeating for a long time. Accordingly, the OLETF mice exhibited the tendency to overeating and overdrinking due to the diabetes at an age of 20 weeks or more.

Meanwhile, in the case of the *Suaeda japonica* juice powder-diet group, the diet intake amount was maintained as it is with little change for the diet period and the water intake amount was slowly increased for the diet period, but significantly lower water intake amount than the control group was exhibited. When considering the above general tendency of the OLETF mice, it was suggested that the *Suaeda japonica* juice powder-diet group exhibited lower diet and water intake amounts than the control group and had an anti-diabetes effect of reducing overeating and overdrinking due to the diabetes.

Further, in the case of the change in weight, the weight of the control group exhibited the tendency to be increased up to an age of 30 weeks and then continuously decreased. It was determined that in the OLETF mice, the weight exhibited the tendency to be rapidly decreased due to the diabetes at the age of 25 weeks or more after obesity. In the *Suaeda japonica* juice powder-diet group, the weight was increased up to an age of 28 weeks and then maintained as it is up to the age of 38 weeks with little change. When considering that there was little change in weight in the *Suaeda japonica* juice powder-diet group as compared with the control group, it was understood that the *Suaeda japonica* juice powder delayed the diabetes voluntarily caused while the OLETF mice grew and thus the reduction of the weight was low.

Verification of Effect of Inhibiting Increase in Blood Glucose

A change in blood glucose was measured at an interval of 2 weeks with respect to the OLETF mice at the age of 26 weeks. The blood glucose was collected from the tail vein of the experimental animals after fasting for one day and measured by using a blood glucose meter (ACCU-Check Active, Roche Diasnotics, Germany). The measured results were illustrated in FIG. 2.

Figure 2:
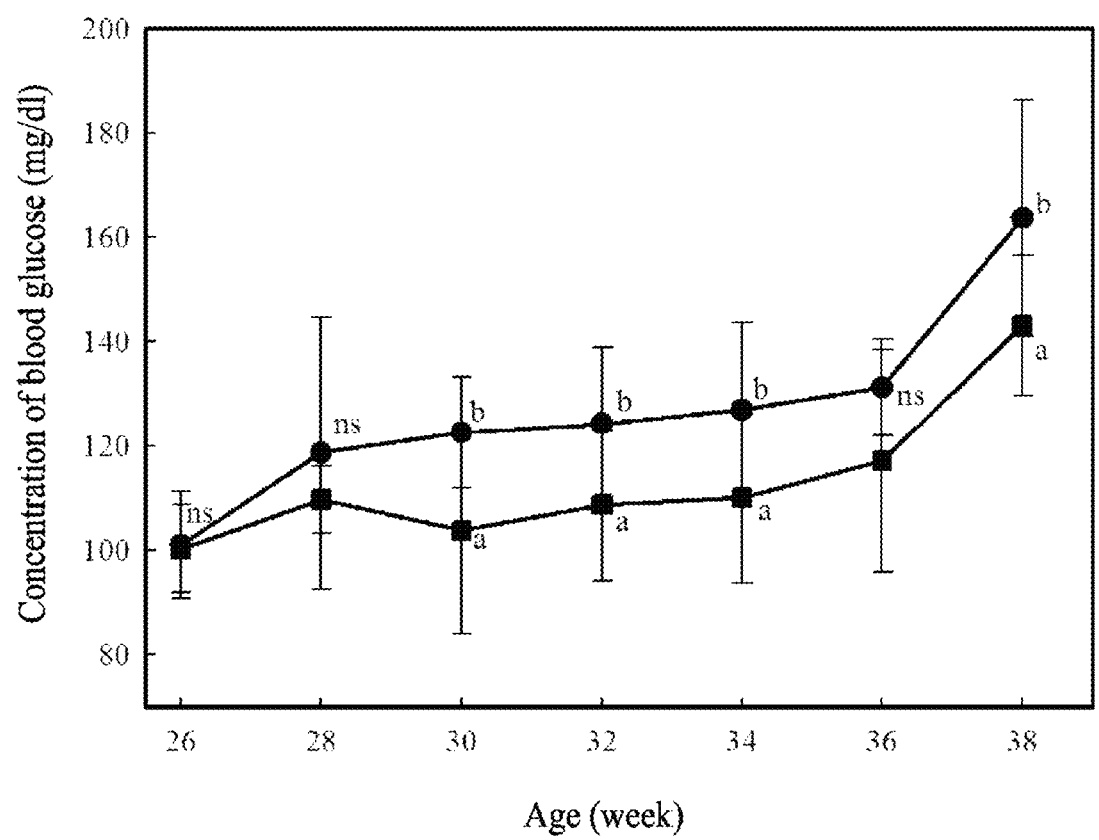
FIG. 2 is a graph illustrating an effect in which the *Suaeda japonica* juice powder inhibits an increase in blood glucose when OLETF mice take the *Suaeda japonica* juice powder according to the embodiment of the present invention.

As illustrated in FIG. 2, in the case of a control group, the blood glucose was increased to 118.6 mg/dL at the age of 28 weeks, gradually increased for the diet period, and then was 163.6 mg/dL at the age of 38 weeks. In the OLETF mice, it was verified that the blood glucose was rapidly increased from the age of 28 weeks and thus, the diabetes was caused due to insulin resistance before the age of 28 weeks, a glucose use rate in the tissue was decreased, and thus the blood glucose was increased. In the *Suaeda japonica* juice powder-diet group, the blood glucose was maintained at 110.1 mg/dL or less up to an age of 34 weeks and then increased from an age of 36 weeks, and finally, the blood glucose of 143.6 mg/dL was exhibited at an age of 38 weeks. In the *Suaeda japonica* juice powder-diet group, a lower increase in blood glucose than the control group was exhibited. Therefore, it was understood that the *Suaeda japonica* juice powder promoted the insulin secretion from the pancreatic cells or increased the glucose use in the tissue to reduce the blood glucose due to the lower blood glucose than the control group. However, in the *Suaeda japonica* juice powder-diet group, the increase in blood glucose was exhibited by promoting the insulin secretion in the pancreatic β-cells due to the diabetes from the age of 38 weeks or rapidly reducing the glucose use in the tissue and thus, it was determined that there was a limit in that the *Suaeda japonica* juice powder inhibited the increase in blood glucose of the OLETF mice at the age of 36 weeks.

Glucose Tolerance Testing Result

A glucose tolerance test was performed at an age of 26 weeks before the diet of the *Suaeda japonica* juice powder in the OLETF mice and at an age of 38 weeks after the diet. After each diet group took the divided feed for 12 weeks and then fasted for one day to orally administrate glucose of 2 g per mouse kg, a glucose tolerance test was performed by investigate the blood collected from the tail vein of the experimental animal at intervals of 30, 60, 120, and 180 minutes. The glucose concentration in the collected blood was measured by using the blood glucose meter (ACCU-Check Active, Roche Diasnotics, Germany). An average blood glucose amount for each diet group measured by the method was calculated and the result was illustrated in FIG. 3.

Figure 3:
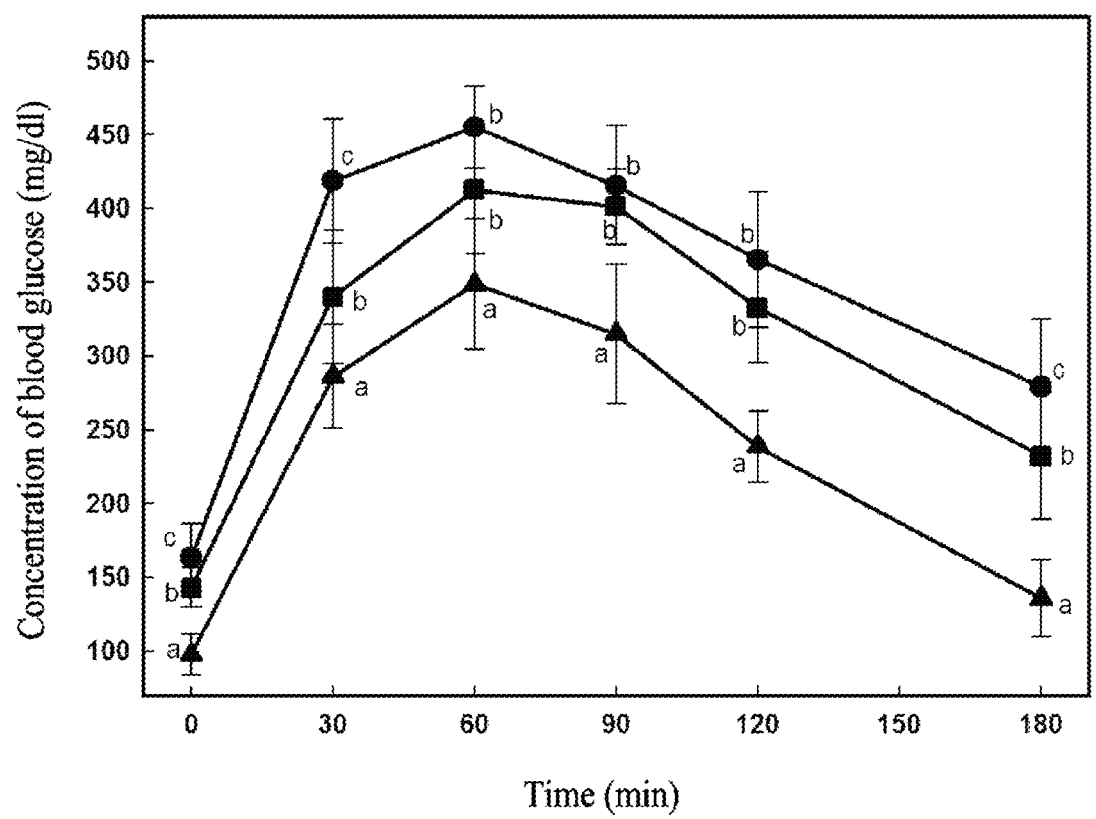
FIG. 3 is a graph illustrating an effect in which the *Suaeda japonica* juice powder improves glucose tolerance when OLETF mice take the *Suaeda japonica* juice powder for 12 weeks according to the embodiment of the present invention.

As illustrated in FIG. 3, in the case of the control group, at the age of 26 weeks before the diet of the *Suaeda japonica* juice powder, when the glucose was orally administrated, a maximum concentration (348.6 mg/dL) of the blood glucose was exhibited after 60 minutes and after 180 minutes, the concentration was decreased to 136 mg/dL, and thus the glucose tolerance testing result of general mice tended to be similar. However, in the control group at the age of 38 weeks after a regular diet, when the glucose was orally administrated, a maximum level (455.1 mg/dL) of the blood glucose was exhibited after 60 minutes and after 180 minutes, the level was exhibited to 279.3 mg/dL, and thus, the blood glucose tended to be slowly decreased. From the result, it was verified that in the OLETF mice, the glucose use in the tissue was decreased due to the diabetes at the age of 38 weeks as compared with at the age of 26 weeks. In the *Suaeda japonica* juice powder-diet group at the age of 38 weeks which took the *Suaeda japonica* juice powder for 12 weeks, when the glucose was administrated, after 60 minutes, the level was highest increased to 415.9 mg/dL and then at the time when 180 minutes elapsed, the level was exhibited as about 233.3 mg/dL. In the *Suaeda japonica* juice powder-diet group which took the *Suaeda japonica* juice powder for 12 weeks, the glucose use was decreased as compared with the control group at the age of 26 weeks, but the glucose use was increased as compared with the control group at the age of 38 weeks. It was seen that there was an improvement effect that the *Suaeda japonica* juice powder increased the glucose use in the tissue of the OLETF mice in which the diabetes was voluntarily induced. Accordingly, from the result, the *Suaeda japonica* juice powder was expected to be useful for preventing the diabetes associated with the insulin resistance.

Effect of Inhibiting Insulin Content and Generation of Glycosylated Hemoglobin (HbA1c)

After OLETF mice took the *Suaeda japonica* juice powder for 12 weeks, a blood collected for determining a change in insulin content in the blood was centrifuged to obtain a serum. The insulin content in the obtained serum was measured by use an ELISA reader set to 450 nm and 620 nm after the serum of 10 L was added and reacted to a mouse insulin Elisa kit (TMB; Shibayagi, Japan). The measured results were illustrated in FIG. 4.

Figure 4:
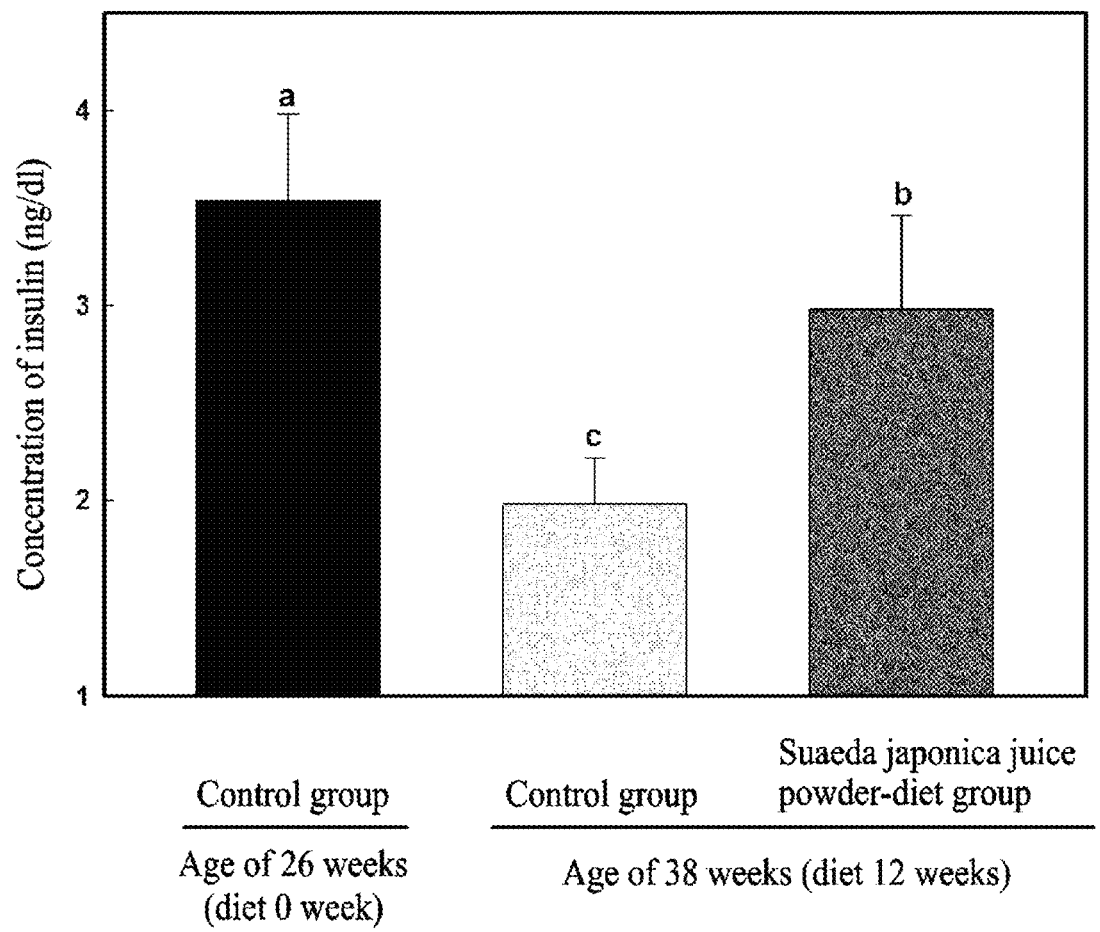
FIG. 4 is a graph illustrating an effect in which the *Suaeda japonica* juice powder maintains the high content of insulin in blood when OLETF mice take the *Suaeda japonica* juice powder for 12 weeks according to the embodiment of the present invention.

As illustrated in FIG. 4, the insulin content of the OLETF mice at the age of 26 weeks was 3.54 mg/mL, but the insulin contents of the control group at the age of 38 weeks and the *Suaeda japonica* juice powder-diet group were decreased to 1.98 mg/mL and 2.98 mg/mL, respectively. The OLETF mice caused the obesity and the diabetes by overeating, in the early stage of the diabetes, the blood glucose in the body was increased and thus the insulin secretion in the pancreatic β-cells tended to be generally increased. However, when the diabetes was continued, the function of the pancreatic β-cells was reduced, and thus, the insulin secretion rate was gradually decreased and the insulin content in the blood was reduced. In the case of the OLETF mice, the reason why the insulin content at the age of 26 weeks was lower than the content at the age of 38 weeks was that the function of the pancreatic β-cells was reduced, and thus, the insulin secretion rate was gradually decreased and the insulin content in the blood was reduced. However, the *Suaeda japonica* juice powder-diet group which took the *Suaeda japonica* juice powder for 12 weeks had the high insulin concentration in blood as compared with the control group at the age of 38 weeks. The *Suaeda japonica* juice powder-diet group had the higher insulin content in blood than the control group and a lower blood glucose level than the control group while taking the *Suaeda japonica* juice powder. It was assumed that the intake of the *Suaeda japonica* juice powder reduced the function deterioration in the pancreatic β-cells of the OLETF mice and delayed the blood insulin degradation.

The glycosylated hemoglobin was formed by irreversibly coupling hemoglobin serving to carry oxygen in the body and the glucose in the blood. The content (%) of glycosylated hemoglobin depends to a period when erythrocytes are exposed to the glucose and the glucose concentration in the blood, and the diabetes patient had a very high level of the blood glucose as the hyperglycemia as compared with a normal person. Particularly, in the blood glucose, a width of the change in the content thereof was very large according to a collection environment such as a food control, but the glycosylated hemoglobin was not changed by an external factor for a short time. Therefore, the concentration of glycosylated hemoglobin (HbA1c) may expect a change in blood glucose for a long time to be widely used to diagnose the diabetes and a complication caused by the diabetes.

Further, the change in the glycosylated hemoglobin content was investigated at the age of 26 weeks before the OLETF mice took the *Suaeda japonica* juice powder and at the age of 38 weeks when the OLETF mice took the *Suaeda japonica* juice powder for 12 weeks. The glycosylated hemoglobin was measured by a NycoCard reader using a NycoCard kit (AXIS-SHIELD PoC AS, Norway) after collecting the blood from the tail vein of the experimental animal. The measured results were illustrated in FIG. 5.

Figure 5:
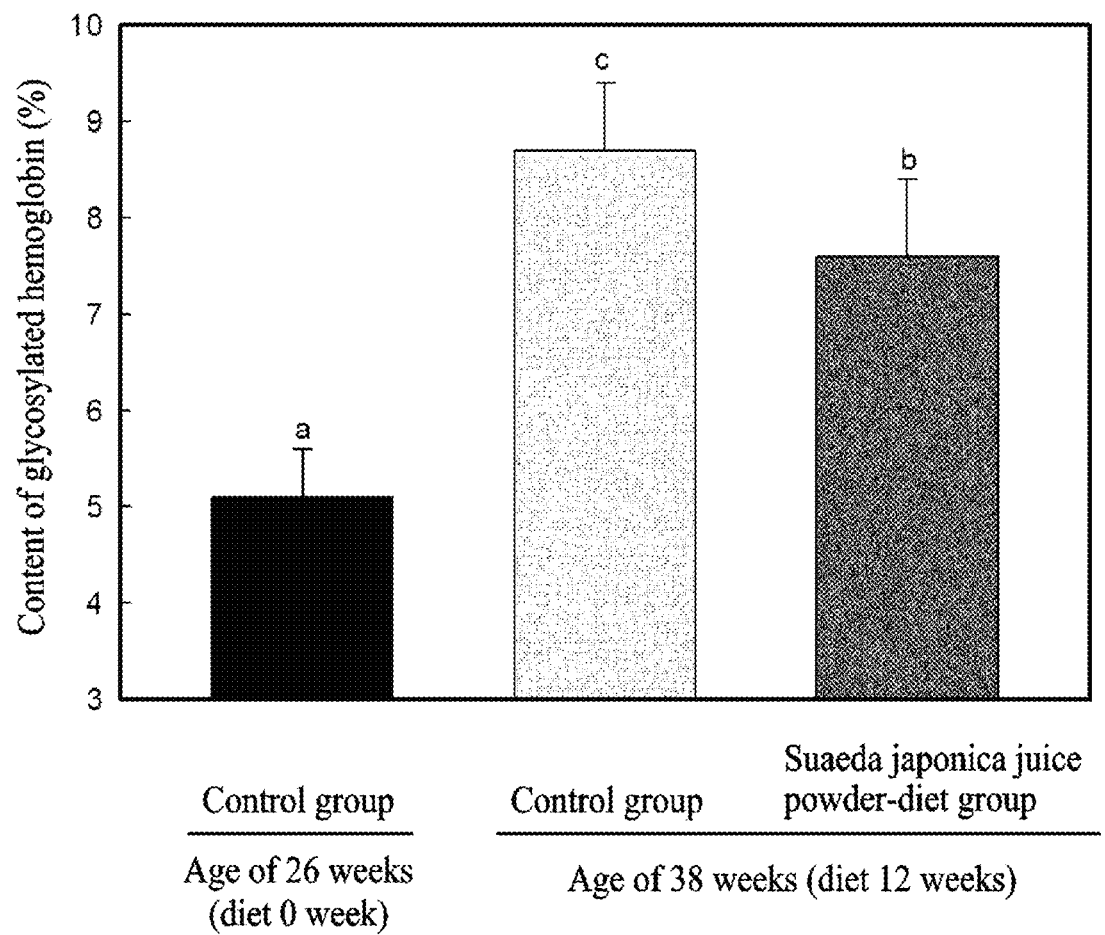
FIG. 5 is a graph verifying that the *Suaeda japonica* juice powder reduces production of glycosylated hemoglobin caused from hyperglycemia when OLETF mice take the *Suaeda japonica* juice powder for 12 weeks according to the embodiment of the present invention.

As illustrated in FIG. 5, the glycosylated hemoglobin content of the OLETF mice at the age of 26 weeks before taking the *Suaeda japonica* juice powder was highly exhibited as compared with a normal mouse, but was a normal value to 5.1%. It was determined that the glycosylated hemoglobin content of the control group at the age of 38 weeks was increased to 8.7% as compared with at the age of 26 weeks and thus, the glycosylated hemoglobin content was increased by reversibly coupling the hemoglobin due to the high glucose concentration in the blood. The glycosylated hemoglobin content of the diet group which took the *Suaeda japonica* juice powder for 12 weeks was significantly low as compared with the control group at the age of 38 weeks. This coincided with the result of the effect of inhibiting the increase in the blood glucose as described above. The high glycosylated hemoglobin content in the blood was associated with the induction of diabetic complications such as retinopathy and nephropathy which may be caused due to the diabetes. It was reported that the diseases such as myocardial infarction, cataract, microvascular diseases, and peripheral vascular diseases were reduced by reducing 1% glycosylated hemoglobin in the blood and finally, the death rate due to the diabetes was reduced. Therefore, it could be seen that the intake of the *Suaeda japonica* juice powder inhibited the production of the glycosylated hemoglobin formed due to the diabetes.

Effect of Promoting Production of Adiponectin

It was known that adiponectin as adipocytokine generated in the fat tissue was associated with the adjustment of the blood glucose and catabolism of the fat. The adiponectin has been exhibited to inhibit obesity, diabetes, atherosclerosis, non-alcoholic fatty liver disease, and the like. Particularly, an increase in the adiponetin concentration in the blood may expect improved insulin sensitivity and recovery of a glucose metabolic function. Accordingly, in order to check the adiponectin content in the blood after the OLETF mice took the *Suaeda japonica* juice powder for 12 weeks, the adiponectin content was measured by a rat high molecular weight adiponetin Elisa kit (Shibayagi Co. Ltd., Japan) in the plasma.

In detail, the plasma of 50 L diluted 50 times was put into an anti-adiponectin-coated ELISA plate and shake-reacted for 2 hours at room temperature, and then 50 L of HRP-conjugated anti-adiponectin was added and reacted for 90 minutes in the same condition. A chromogenic substrate reagent of 50 L was added to the reaction solution and reacted for 30 minutes, and then, the reaction stopped with 50 L of 1M H2SO4. In the final reaction solution, absorptance was measured by using a spectrophotometer at 450 nm and the adiponectin content in the blood was calculated by using a standard curve prepared with a standard substance. The measured results were illustrated in FIG. 6.

Figure 6:
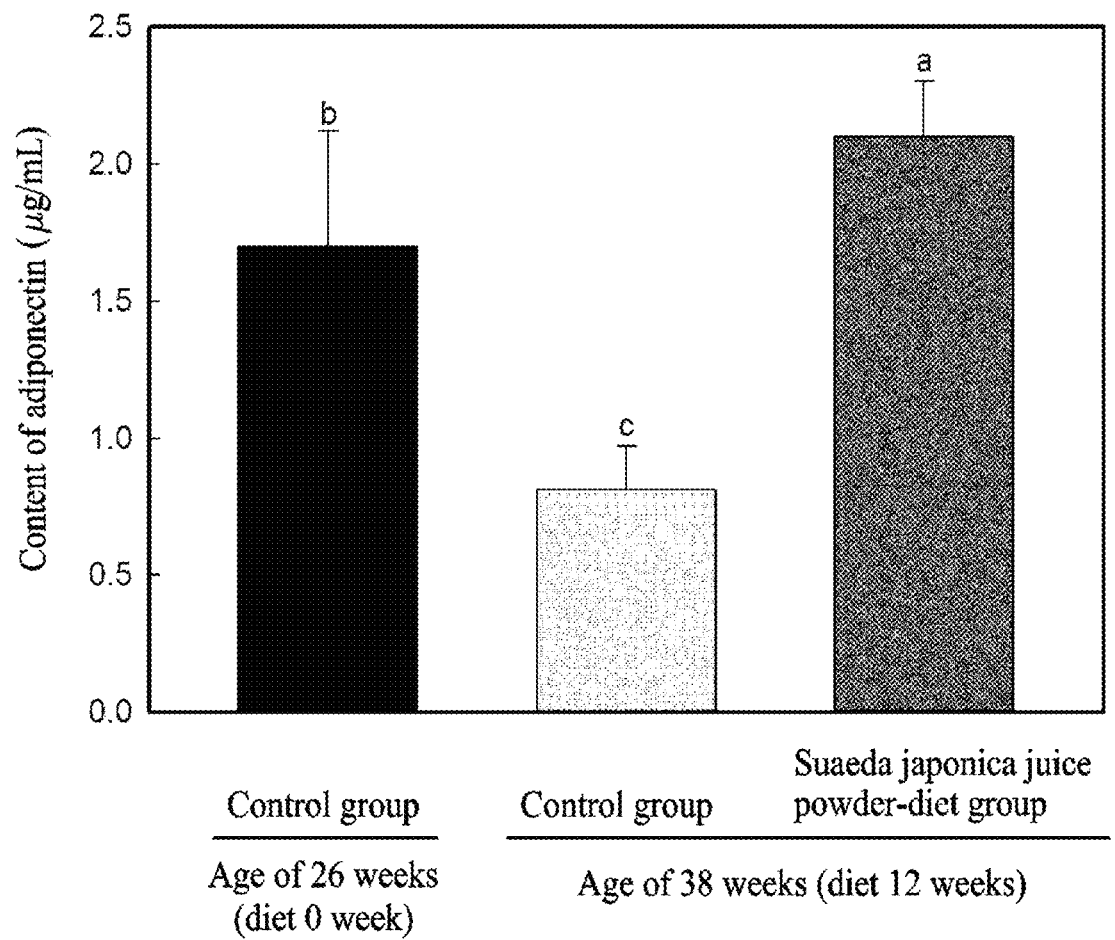
FIG. 6 is a graph illustrating an effect in which the *Suaeda japonica* juice powder facilitates generation of adiponectin suppressing obesity and diabetes when OLETF mice take the *Suaeda japonica* juice powder for 12 weeks according to the embodiment of the present invention.

As illustrated in FIG. 6, the adiponectin content in the blood of the OLETF mice at the age of 26 weeks was 1.7 g/mL, but decreased to 0.81 g/mL at the age of 38 weeks by two times or more. It was suggested that in the OLETF mice, while the obesity and the diabetes proceeded, a production amount of TNF-α which was known as an antagonist of adiponetin in the fatty tissue was increased due to oxidative stress and the production of adiponectin was relatively reduced. Interestingly, the *Suaeda japonica* juice powder-diet group which took the *Suaeda japonica* juice powder for 12 weeks had a very high value of adiponetin in the blood as compared with the control group at the age of 38 weeks and had a higher value than the control group at the age of 26 weeks before taking the *Suaeda japonica* juice powder. It was understood that the *Suaeda japonica* juice powder lowered the oxidative stress in the fatty tissue to inhibit the production of the TNF-α and promoted the adiponetin secretion or delayed the adiponetin degradation in the blood to have the high adiponetin value. Accordingly, it can be seen that the *Suaeda japonica* juice powder highly maintained the adiponectin content in the blood to improve the insulin sensitivity and recover the glucose metabolic function.

When summarizing the result, it was verified that the intake of the *Suaeda japonica* juice powder reduced the blood glucose increased due to the obesity and the diabetes voluntarily caused while the OLETF mice grew. Further, in the *Suaeda japonica* juice powder-diet group, the contents of the glycosylated hemoglobin, the blood insulin, and the adiponectin were high and the glucose tolerance was improved as compared with the control group. Therefore, it was determined that the *Suaeda japonica* juice powder had an effect of preventing diseases such as diabetes associated with the insulin resistance, and thus, the effect of preventing the diseases was caused by an organic compound having the effect of preventing the diabetes such as improved signal transfer of insulin included in the *Suaeda japonica* juice powder.

Effect of Protecting Pancreatic β-Cells of *Suaeda japonica* Juice Powder in OLETF Mice After OLETF mice at the age of 26 weeks in which insulin resistance was caused took the *Suaeda japonica* juice powder for 12 weeks, the pancreas was separated in order to check a histological type of the pancreatic β-cells. The analysis of the histological type of the pancreatic β-cells was performed by an avidin-biotin-perosidase (ABC) method. That is, the collected pancreatic tissue was embedded with paraffin and then the pancreatic tissue was segmented. Xylene was treated in the segmented tissue, and then the treated tissue was hydrated with ethanol and washed with distilled water and a phosphate solution. Antigen retrieval was performed using a microwave in the hydrated tissue and then a normal goat serum (NGS) was treated. The pancreatic tissue segment reacted with a first insulin antibody (guinea pig polyclonal to insulin) and then performed antigen-antibody reaction by using a second insulin antibody (goat anti-gp. Ab IgG). The tissue through the antigen-antibody reaction was treated with a mixed solution (ABC kit) of avidin DH and biotinylated enzyme and treated with diamin-obenzidine (DAB) including $H_2O_2$, and then formation of a phenazine polymer was observed by a microscope.

Figure 7:
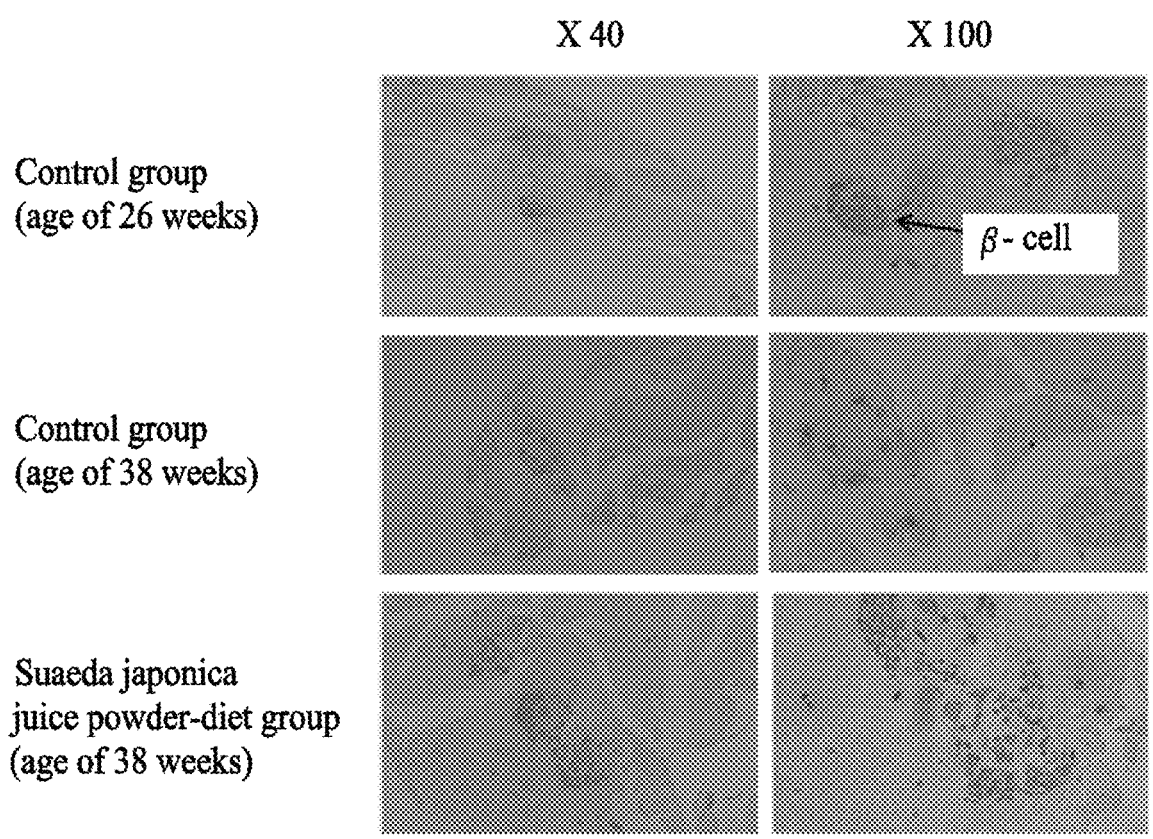
FIG. 7 illustrates a tissue form of pancreatic β-cells which verify a protective effect on the pancreatic β-cells secreting insulin of the *Suaeda japonica* juice powder when OLETF mice take the *Suaeda japonica* juice powder for 12 weeks according to the embodiment of the present invention.

As illustrated in FIG. 7, the pancreatic β-cells of the OLETF mice at the age of 26 weeks were not almost destroyed. However, it was verified that most of the pancreatic β-cells of the OLETF mice at the age of 38 weeks in which the diabetes proceeded for 12 weeks were destroyed.

It was understood that when the second type of diabetes was continued through the insulin resistance, the tissue of the pancreatic β-cells was destroyed due to the excessive secretion of insulin. When the OLETF mice in which the diabetes was caused due to the insulin resistance took the *Suaeda japonica* juice powder for 12 weeks, the destruction degree of the pancreatic β-cells of the mice at the age of 38 weeks was significantly lower than that of the control group at the age of 38 weeks.

In the present invention, it was verified that the *Suaeda japonica* juice powder delayed the progress of the second type of diabetes and prevented the pancreatic β-cells destruction through an animal experiment.

What is claimed is:
1. A tablet or capsule consisting essentially of *Suaeda japonica* extract, dextrin, lactose and talc.

* * * * *